(12) United States Patent
Addison et al.

(10) Patent No.: US 6,566,577 B1
(45) Date of Patent: May 20, 2003

(54) WOUND DRESSINGS HAVING LOW ADHERENCY

(75) Inventors: Deborah Addison, Via Lancaster (GB); James Sebastian Mellor, North Yorkshire (GB); Martin William Stow, North Yorkshire (GB); Maurice Charles Biott, West Yorkshire (GB)

(73) Assignee: Johnson & Johnson Medical Limited (GB)

( * ) Notice: Subject to any disclaimer, the term of this patent is extended or adjusted under 35 U.S.C. 154(b) by 0 days.

(21) Appl. No.: 09/937,039
(22) PCT Filed: Mar. 23, 2000
(86) PCT No.: PCT/GB00/01105
§ 371 (c)(1),
(2), (4) Date: Feb. 14, 2002
(87) PCT Pub. No.: WO00/56256
PCT Pub. Date: Sep. 28, 2000

(30) Foreign Application Priority Data

Mar. 24, 1999 (GB) ................................ 9906809

(51) Int. Cl.⁷ ................................................ A61F 13/00
(52) U.S. Cl. ...................... 602/56; 602/43; 604/304; 604/307; 604/367; 604/369
(58) Field of Search ............... 602/41–43, 46–47, 602/56, 58–61; 604/304, 307, 367, 369

(56) References Cited

U.S. PATENT DOCUMENTS 3,054,148 A    9/1962   Zimmerli ................... 18/56
3,967,623 A  * 7/1976   Butterworth et al.
4,655,209 A  * 4/1987   Scott

FOREIGN PATENT DOCUMENTS

| DE | 645 698   | 5/1937  |
|----|-----------|---------|
| EP | 0 541 391 | 6/1998  |
| GB | 1 280 631 | 7/1972  |
| GB | 1 292 133 | 10/1972 |
| GB | 1 526 778 | 9/1978  |
| GB | 2 074 209 | 10/1981 |
| GB | 2 085 305 | 4/1982  |

\* cited by examiner

*Primary Examiner*—Nicholas D. Lucchesi
*Assistant Examiner*—Lalita M Hamilton
(74) *Attorney, Agent, or Firm*—Woodcock Washburn LLP (57) ABSTRACT

The invention provides wound dressings, in particular wound dressings of low- or non-exuding wounds a bleeding wounds. The wound dressings are of the island type, having as adhesive-coated backing sheet (6) and an absorbent island (9) supported on the backing sheet. The island (9) comprises a layer (2) of liquid absorbent material enclosed in an envelope of textured perforated thermoplastic film. The film (3) at one side of the island (9) presents a ribbed or embossed perforated surface having low adherency to the wound. The film island an the rear surface of the envelope is perforated and smoothed to provide good attachment to the backing sheet (6) and controlled water vapor transmission rate. The invention also provides a method of manufacture of the wound dressings according to the invention, according to which the absorbent layer (2) is wrapped in a textured perforated thermoplastic film, and the film on the rear face of the envelope is then preferably smoothed by blowing hot air onto it.

31 Claims, 3 Drawing Sheets

WOUND DRESSINGS HAVING LOW ADHERENCY

The present invention relates to wound dressings, and in particular to such dressings having low adherency for use on low- to non-exuding wounds. The present invention also relates to processes for the preparation of such wound dressings, and to an apparatus specifically adapted for use in such processes.

Wound dressings are known that consist of a layer of absorbent material, such as an absorbent gauze or foam layer, wherein the layer is supported on an adhesive-coated semipermeable backing sheet. An adhesive-coated margin of the backing sheet extends outwardly from the edges of the absorbent layer for attachment of the dressing over a wound by adhesion to the skin surrounding the wound. The absorbent layer serves to absorb wound exudate. Such dressings are commonly known as island wound dressings.

A difficulty that can arise with island wound dressings is that most absorbent layers, such as nonwoven fibrous webs, are somewhat adherent to a wound surface, and is particular tend to dry out and adhere to wounds having a low rate of exudate production, or to non-exuding wounds. Adherence can also be a problem with bleeding wounds because of clot formation in the dressing. Adherence is unfavorable for wound healing, and can result in discomfort when the island wound dressing is changed. There is a further risk that the absorbent island could shed fibers or particles into the wound.

Another drawback of such dressings is that many absorbent island materials, such as nonwoven fibrous webs, show relatively poor attachment to the adhesive coating of the backing sheet. There is therefore a risk that the absorbent island can detach from the backing sheet. The problem of poor attachment of the island to the backing sheet is exacerbated when attempts are made to render the island less adherent to the wound, for example by using a bonded or coated island.

GB-A-2074029 describes island-type wound dressings having a top sheet of perforated polytetrafluoroethylene (PTFE) film covering the absorbent layer. The PTFE film provides a non-adherent wound contacting layer for the dressing.

GB-A-2085305 describes wound dressings in which the absorbent island is entirely embraced by a cellular plastics film having perforations which have been produced by passing electrical discharges therethrough. The film may be provided with a layer of adhesive for attachment around a wound.

GB-A-1526778 describes wound dressings comprising an absorbent layer and a top sheet over the absorbent lays, wherein the top sheet is a textured perforated plastic film that provides improved passage of fluids into the absorbent layer.

It is an object of the present invention to provides improved wound dressings, in particular improved island-type wound dressings, especially suitable for the treatment of wounds that product little or no exudate and for bleeding wounds.

It is a further object of the present invention to provide an improved wound dressing that has low adherency to the wound surface, and preferably substantially no adherency to the wound surface.

Is a further object of the present invention to provide an improved wound dressing that provides improved securement of the absorbent island to the backing sheet.

Is a further object of the present invention to provide as improved wound dressing that has less tendency to cause low- to non-exuding wounds and bleeding wounds to dry out and form scabs, and to optimise wound healing conditions under the wound dressing.

If a further object of the present invention to provides an improved wound dressing that has reduced tendency to shed fibers or particles into the wound during treatment.

The present invention provides a wound dressing comprising:

as absorbent layer;

an envelope formed from thermoplastic film enclosing the absorbent layer, wherein the film has a textured perforated surface on a front side of the envelope and a smoothed perforated surface on a rear side of the envelope;

a semipermeable backing sheet covering the rear side of the envelope and, extending outwardly therefrom; and a layer of adhesive on the backing sheet adjacent to the rear side of the envelope and bonding the rear side of the envelope to the backing sheet.

The wound dressings according to the present invention are especially suitable as wound dressings for use on low- or non-exuding wounds of bleeding wounds. The area of the absorbent layer is typically in the range of from 1 $cm^2$ to 200 $cm^2$, more preferably from 4 $cm^2$ to 100 $cm^2$.

The absorbent layer may be any of the layers conventionally used for absorbing wound fluids, serum or blood in the wound healing art, including gauzes, nonwoven fabrics, superabsorbents, hydrogels and mixtures thereof. Preferably, the absorbent layer comprises a layer of absorbent foam, such as an open celled hydrophilic polyurethane foam prepared in accordance with EP-A-0541391, the entire content of which is expressly incorporated herein by reference. In other embodiments, the absorbent layer may be a nonwoven fibrous web, for example a carded web of viscose staple fibers. Since the wound dressings according to the present invention are generally only intended for use on low- or non-exuding wounds or bleeding wounds, it follows that the thickness and absorbency of the absorbent layer is preferably not very high. Preferably, the basis weight of the absorbent layer is in the range of 50–500 $g/m^2$, more preferably 100–400 $g/m^2$. The uncompressed thickness of the absorbent layer is preferably in the range of from 0.5 mm to 5 mm, more preferably 1 mm to 4 mm. The free (uncompressed) liquid absorbency measured for physiological saline is preferably in the range of 5 to 30 g/g at 25° C.

The thermoplastic film enclosing the absorbent layer may be formed from substantially any thermoplastic film-forming polymer. Preferably, the polymer is conformable but not substantially elastomeric. Preferably, the polymer is hydrophilic. Suitable polymers include, but are not limited to, polyethylene, polypropylene, polyester, polyamides such as nylons, fluoropolymers such as polyvinylidene fluoride (PVDF) or polytetrafluoroethylene (PTFE), and mixtures thereof. The currently preferred film forming thermoplastic polymer is ethylene methyl acrylate (EMA).

The thermoplastic film is textured and perforated. The term "textured" indicates that the film is patterned in relief, for example, patterned with protruding ridges or nubbles, for example by embossing. The texturing renders the film less adherent to a wound bed. The ridges island nubbles are preferably rounded, and preferably project by 0.1 to 1.5 mm above the median plane of the film surface. More preferably they project by 0.2 to 1.0 mm above the median plane of the film.

Preferably, the thermoplastic film is both textured and perforated by means of mesh perforation. In this method, the film is supported on a reticulated mesh surface and heated to its softening temperature. Suction is then applied through the mesh, or air is blown onto the film above the mesh, which results in impression of the mesh into the film and the formation of perforations in the film at the interstices of the mesh. Mesh perforation technique are described in more detail in U.S. Pat. No. 3,054,148, the entire content of which is expressly incorporated herein by reference.

Preferably, the thermoplastic film has from 5 to 50 perforations/cm$^2$, more preferably from 10 to 30 perforations/cm$^2$. Preferably, the perforations have an area of from 0.01 to 2.0 mm$^2$. The hole-to-land ratio, defined as the ratio of the total area of the perforations to the total area of the film less the area of the perforations, both areas being viewed in plans projection, is preferably from 0.01 to 1.0, more preferably from 0.05 to 0.5 and most preferably from 0.1 to 0.3.

The thermoplastic film should be as thin as possible consistent with the need for physical integrity during manufacture and use. Typically, the film has a basis weight of from 1 to 500 g/m$^2$, preferably island 10 to 200 g/m$^2$.

The thermoplastic film is formed into an envelope for the absorbent layer. The term "envelope" signifies that the front and back faces of the absorbent layer are substantially completely covered (substantially completely embraced) by the thermoplastic film. For example, two sheets of the thermoplastic film may be located above and below the absorbent layer substantially covering the top and bottom faces of the absorbent layer, the two sheets being bonded along two or more edges to form the envelope. However, preferably, the envelope is formed from a single piece of the thermoplastic film that has been folded wound the absorbent layer sa that opposed longitudinal edges of the film overlap, the overlapping edges being bonded together in the overlapping region, typically with hot melt adhesive or by heat bonding, to form the envelope. Such envelopes may be made by minor modification of conventional form-fill-seal equipment, as described further below.

The backing sheet is semipermeable. That is to say, the backing sheet is permeable to water vapour, but not permeable liquid water. Preferably, the backing sheet is also microorganism-impermeable. Suitable continuous conformable backing sheets will have a moisture vapour transmission rate (MVTR) of the backing sheet alone of 300 to 5000 g/m$^2$/24 hrs, preferably 500 to 2000 g/m$^2$/24 hrs at 37.5° C. at 100% to 10% relative humidity difference. The backing sheet thickness is preferably in the range of 10 to 1000 micrometers, more preferably 100 to 500 micrometers.

The MVTR of the dressing according to the present invention as a whole is lower than that of the backing sheet alone, because the thermoplastic film envelope partially obstructs moisture transfer through the dressing. Preferably, the MVTR of the dressing (measured across the island portion of the dressing) is from 20% to 80% of the MVTR of the backing sheet alone, more preferably from 20% to 60% thereof, and most preferably about 40% thereof. It has been found that such moisture vapor transmission rates allow the wound under the dressing to heal under moist conditions without causing the skin surrounding the wound to macerate.

Suitable polymers for forming the backing sheet include polyurethanes and poly alkoxyalkyl acrylates and methacrylates such as those disclosed in GB-A-1280631. Preferably, the backing sheet comprises a continuous layer of a high density blocked polyurethane foam that is predominantly closed-cell. A suitable backing sheet material is the polyurethane film available under the Registered Trade Mark ESTANE 5714F.

The adhesive layer should be moisture vapor transmitting and/or patterned to allow passage of water vapor therethrough. The adhesive layer is preferably a continuous moisture vapor transmitting, pressure-sensitive adhesive layer of the type conventionally used for island-type wound dressings, for example, a pressure sensitive adhesive based on acrylate ester copolymers, polyvinyl ethyl ether and polyurethane as described for example in GB-A-1280631. The basis weight of the adhesive layer is preferably 20 to 250 g/m$^2$, and more preferably 50 to 150 g/m$^2$. Polyurethane-based pressure sensitive adhesives are preferred.

Preferably, the adhesive layer extends outwardly from the absorbent layer and the envelope to form an adhesive-coated margin an the backing sheet around the adhesive layer as in a conventional island dressing. Preferably, the wound dressings according to the present invention further comprise a release coated layer to protect the adhesive and absorbent layer before use. Preferably, the cover layer comprises silicone release-coated paper.

Preferably, the wound dressings according to the present invention are sterile, and are packaged in a microorganism-impermeable container, preferably a pouch.

The thermoplastic film enclosing the absorbent layer has a smoothed perforated surface on the rear side of the envelope. That is to say, the thermoplastic film on the rear side of the envelope (that is to say the side that faces away from the wound surface and towards the backing sheet in use) is smoother than the thermoplastic film covering the front (wound contacting) side of the envelope. Preferably, the surface roughness or degree of texturization of the rear side of the envelope is no more than 80% of the surface roughness or degree of texturization of the front side of the envelope, more preferably no more than 70% thereof, still more preferably no more than 50% thereof, and even more preferably no more than 30% thereof.

The textured wound contacting from surface of the envelope provides low adherence combined with good wicking of liquid from the wound into the absorbent layer through the perforated thermoplastic film. In contrast the smoothed thermoplastic film layer on the rear side of the envelope provides excellent adhesion to the adhesive layer on the backing sheet, whilst retaining perforations that enable water vapour to diffuse out through the semipermeable backing sheet, thereby preventing saturation of the absorbent layer. The term "smoothed" signifies that the rear thermoplastic film lays has less surface texturing (roughness, unevenness) than the front thermoplastic film layer of the envelope. Preferably, substantially none of the smoothed film surface projects 100 $\mu$m or more above the median plane of the smoothed film surface. More preferably substantially none of the smoothed film surface projects more than 25 $\mu$m above she median plane of the smoothed film surface.

The wound dressings according to the present invention provide a number of advantages an wound dressings for low- or non-exuding wounds or bleeding wounds. Firstly, the textured thermoplastic film wound facing layer (top sheet) is substantially or completely non-adherent by virtue of in non-fibrous composition and textured surface. Wound exudate liquid can pass through the perforated top sheet into the absorbent layer, but the hole-to-land ratio of the top sheet is low enough to prevent the wound becoming excessively dried out. The perforated top sheet also prevents fibers or particles of the absorbent layer from shedding into the wound.

The envelope structure further provides for secure attachment of the absorbent layer to the backing sheet. This is because the smoothed rear surface of the envelope ensures reliable attachment of the envelope to the backing sheet. Furthermore, the hole-to-land ratio an hereinbefore defined of the smoothed rear film enables the rate of water vapour diffusion through the backing sheet to be controlled so an to prevent drying out of the wound. Finally, the wound dressings according to the present invention are especially easy to manufacture using conventional equipment, as will be described is more detail below.

The present invention also provides a process for the production of a wound dressing comprising the steps of:

providing a layer of absorbent material;

wrapping the lays in an envelope of a textured perforated thermoplastic film; followed by smoothing the thermoplastic film on one side of the envelope; and applying an adhesive-coated backing sheer onto the smoothed thermoplastic film on the said one side of the envelope.

Preferably, the process according to the present invention is specifically adapted for the manufacture of a wound dressing is accordance with the present invention.

Preferably, the step of wrapping the absorbent layer is an envelope of a textured perforated thermoplastic film comprises wrapping a single sheet of the thermoplastic film around the absorbent layer so that two opposed edges of the thermoplastic film overlap longitudinally, and forming a seal along said overlap, for example with hot melt adhesive or by heat sealing. This step of wrapping and sealing can be carried out on modified form-fill-seal equipment. Preferably, the steps of wrapping and sealing are carried out continuously on the form-fill-seal equipment, in which case the steps are followed by, the step of cutting the envelope into lengths for use as islands in the island-type dressings.

Normally the front and back faces of the envelope will be formed from the same textured perforated thermoplastic film. As a result, the back surface of the envelope needs to be smoothed subsequently to the wrapping step. In practice, the step of smoothing is difficult to perform, since hot rolling or pressing the thermoplastic film frequently results in adhesion of the film to the roller or press and/or undesirable penetration or the softened hot film into the absorbent material unless the conditions are carefully controlled.

It is therefore a further novel feature of the process according to the present invention that the step of smoothing the textured perforated thermoplastic film is preferably carried out by blowing hot air onto one side of the envelope containing the absorbent material is a controlled fashion. The step of blowing hot air onto the film causes the film to flatten and smooth out, without flowing into the absorbent material, and without any need to apply mechanical pressure to the film. Preferably, the temperature of the film is monitored, and the temperature of the hot air being blown onto the film is continuously optimised in response to the measured temperature of the film.

In the continuous process hereinbefore described, the step of blowing hot air onto one surface of the envelope to flatten the film is preferably carried out after continuous formation of the envelope on form-fill-seal equipment, but before cutting the envelope into lengths. Preferably, there is a cooling step intermediate the smoothing step and the cutting step since otherwise the hot film may stick to the cutting knife.

The present invention further provides an apparatus specifically adapted for carrying out a process according to the present invention as hereinbefore described. The apparatus comprises:

a conveyor for conveying a lays of absorbent material enclosed between two layers of performed textured thermoplastic film;

a hot air blower configured to blow hot air onto one of the layers of thermoplastic film to soften and flatten the said one of the layers, thereby smoothing said one of said layers;

a temperature sensor to measure the temperature of the said one of the layers adjacent to the hot air blower; and control means connected to the temperature sensor to regulate the conveyer and/or the hot air blower is response to signals from the temperature sensor.

The conveyor may be any vertical of horizontal conveying means, including a conveyor belt. The hot air blown is preferably a heat gun, preferably adjustable to blow hot air in a temperature range above the softening temperature of the thermoplastic film but below its melting temperature. For example, for a ethylene methyl acrylate (EMA) film, the hot air is preferably blower at a temperature in the range of from 110 to 160° C. The temperature sensor is preferably an infrared radiant temperature sensor located adjacent to the hot film just downstream from the hot air blower. The control means is preferably connected to the heater input of the hot air blower, whereby the temperature of the hot air can be controlled continuously to optimise the smoothing and production speed.

Specific embodiments of the products, process and apparatus according to the present invention will now be described further, by way of example, with reference to the accompanying drawings, in which.

Figure 1:
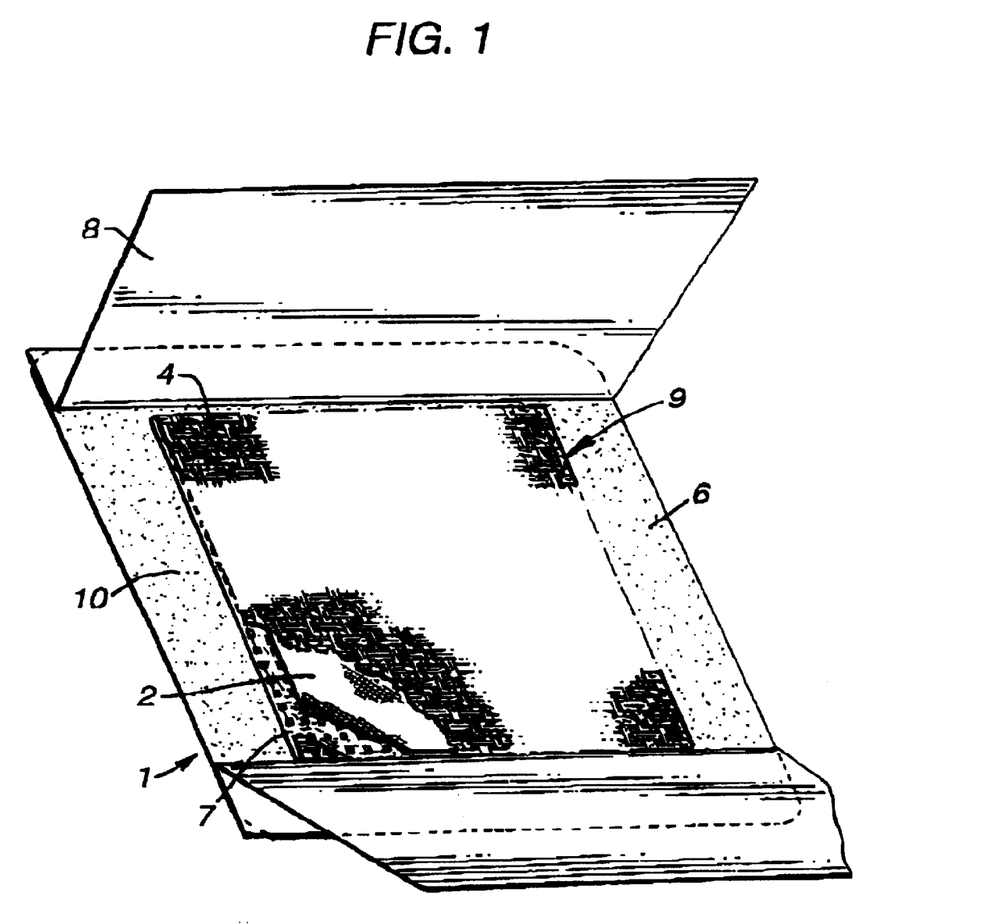
FIG. 1 shows a perspective view of an island-type wound dressing according to the present invention, with the cover sheet partially peeled back and the island partially cut away to show hidden details.

Referring to FIG. 1, the wound dressing 1 according to the present invention comprises an absorbent island 9 supported on an adhesive-coated backing sheet 6 that extends beyond the edges of the island 9 to provide and adhesive-coated margin 10 for attachment of the dressing 1 over a wound. The island comprises an absorbent layer 2, consisting of a hydrophilic polyurethane foam layer, for example prepared as described in EP-A-0541391, having a basis weight of 350 g/m$^2$ and a thickness of approximately 1.5 mm. In other embodiments the absorbent layer 2 is a nonwoven fabric of viscose staple fibers having a basis weight of about 150 g/m$^2$. The absorbent layer 2 is enclosed in an envelope formed from a single sheet of mesh perforated EMA film. The EMA film has a basis of 50 g/m$^2$, and contains 25 perforations/cm$^2$, each perforation having dimensions of approximately 1 mm×1 mm. The perforations are arranged in a square grid pattern, corresponding to the pattern of interstices on the mesh used for perforation of the film. The hole to land ratio of the film is about 0.1. The envelope is formed from a single piece of EMA film that has been wrapped around the absorbent layer (EMA) and bonded using a hot-melt adhesive along a longitudinal overlap (not shown) of opposed edges of the film on the back face of the envelope.

Figure 2:
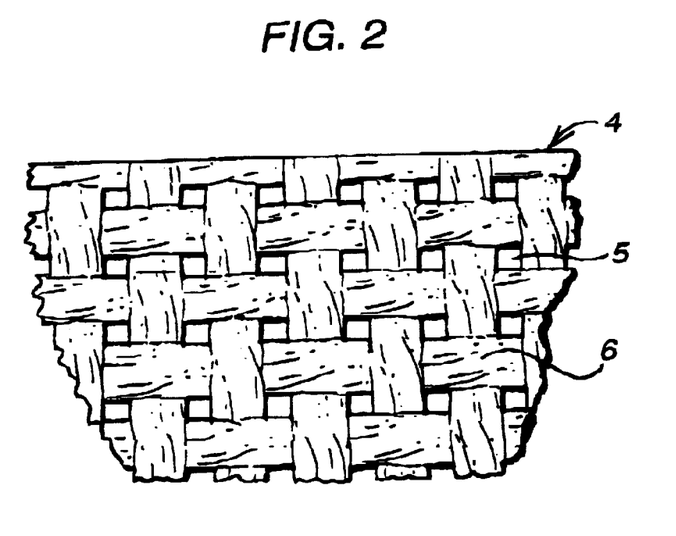
FIG. 2 shows a view on B of FIG. 1, being a top plan view or part of the front surface of the wound contacting layer of the perforated film envelope.

The front face 4 of the EMA film envelope comprises the original mesh-perforated surface of the EMA film, with the back of the film (i.e. the surface to which suction was applied in the mesh perforating step) facing the absorbent layer 2 and the front surface of the EMA film facing outwardly to form the wound contacting surface of the wound dressing 1. This is shown more clearly in FIGS. 2 and 4. The perforations 5 provide rapid passage of free fluid such as wound fluid into the absorbent layer but the hole-to-land ratio of the film is low enough to avoid excessive dehydration or the wound surface. The land portions 6 of the mesh perforated EMA film are embossed in relief with the pattern of the mesh a shown in FIG. 2. This embossed, textured surface is very non-adherent and wound friendly.

Figure 3:
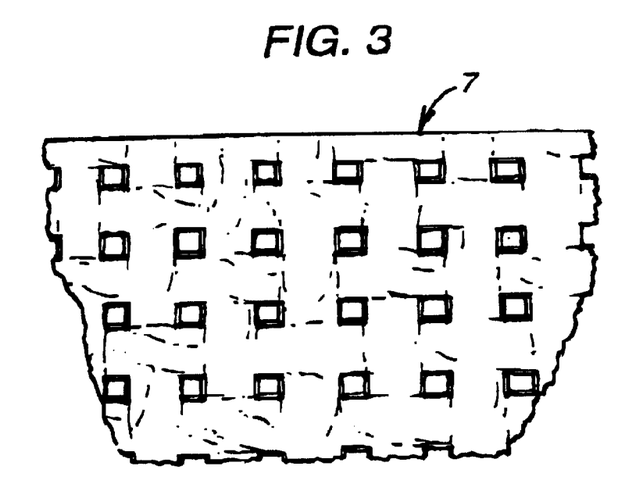
FIG. 3 shows a view on A of FIG. 1, being a bottom plan view of the rear face of the perforated film envelope after smoothing.
Figure 4:
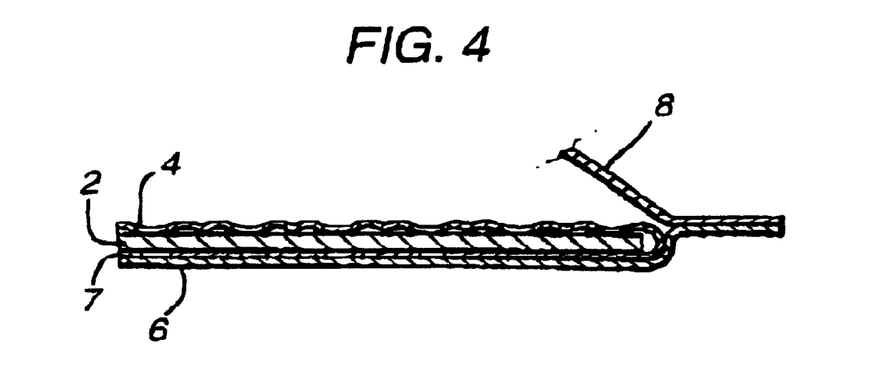
FIG. 4 shows a partial cross-section through the dressing of FIG. 1 along the section line IV—IV.
Figure 5:
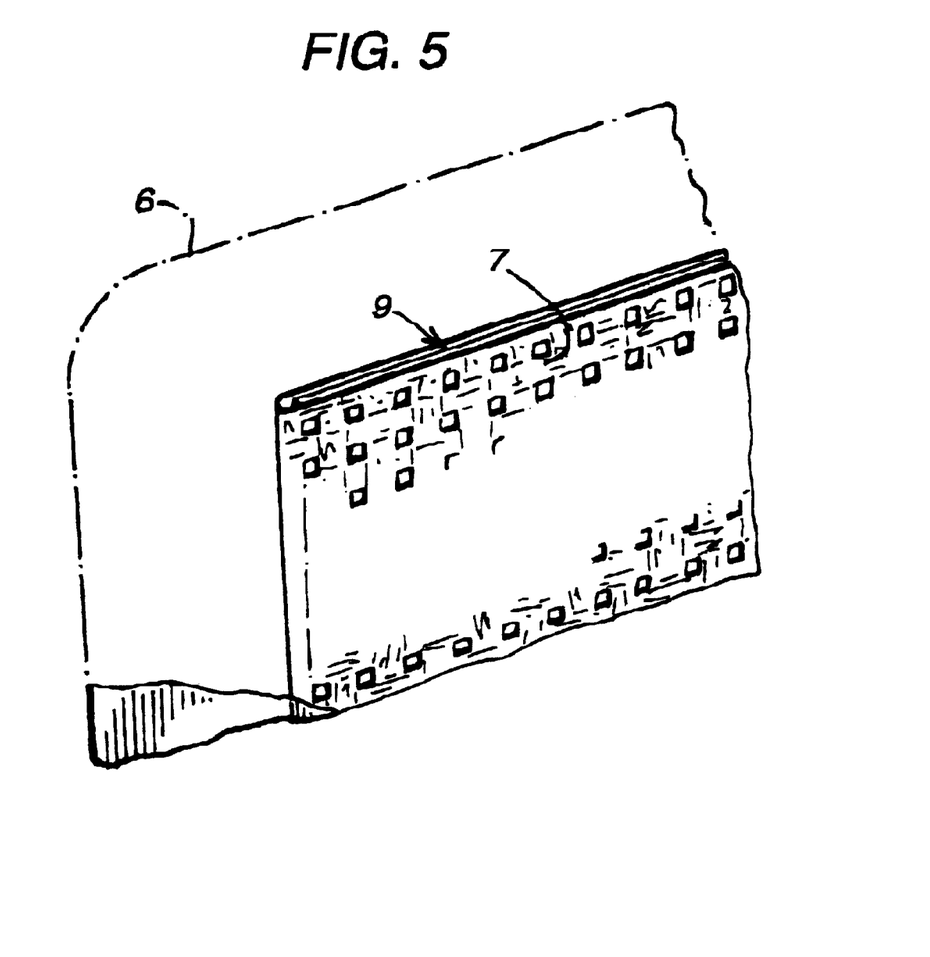
FIG. 5 shows a partial perspective view of the rear of the dressing of FIG. 1.

The back surface 1 of the EMA film has been smoothed to a substantially flat, perforated film an described further hereinbelow and as shown in FIGS. 3, 4 and 5. The smoothed surface of the back surface 1 provides improved adhesion to the adhesive-coated backing sheet.

The wound dressing further comprises a backing sheet 6 formed from a substantially closed-cell microporous polyurethane foam having a water vapor transmission rate as hereinbefore defined of 1200–1300 g/m$^2$/24 hrs. The backing sheet is coated on its lower surface with a continuous layer of water vapor permeably, pressure-sensitive polyurethane adhesive is an amount of 90–110 g/m$^2$.

The wound contacting surface of the dressing is covered by two silicone release-coated protective sheets 8 that are folded to allow easy removal of the sheets 8 before use, as shows in FIGS. 1 and 5. The dressing is sterilised by gamma-irradiation and packaged is a microorganism-impermeable pouch (not shown).

The wound dressing according to the present invention is prepared as follows. A continuous strip of the polyurethane foam is wrapped is the EMA perforated film using form-fill-seal equipment. The continuous, wrapped envelope is then passed by a conveyor underneath a hot air gun that blown hot air onto the rear side of the envelope to soften and smooth the film on the rear side of the envelope. The absorbent layer 2 provides sufficient thermal insulation to prevent the heat (EMA) the hot air gun from significantly softening and smoothing the textured film on the front face of the envelope.

The temperature of the gun is regulated by a control means connected to an infrared-type thermocouple sensor mounted in front of the gun to measure the temperature of the thermoplastic film on the rear side of the envelope. The sensor provides feedback to the control means to achieve continuous control or the film temperature for optimum smoothing of the rear surface of (EMA) envelope. For an EMA film this corresponds to hot air preferably at a temperature of 110–160° C.

After smoothing, the envelope is allowed to cool and is then cut into lengths, each length corresponding to an island for a wound dressing according to the present invention. The islands are then applied to the adhesive-coated backing sheet with the smoothed rear side of the envelope contacting the adhesive, followed by application of the silicone coated protective sheets, sterilisation and packaging.

The above examples have been described for the purpose of illustration only. Many other embodiments or the present invention falling within the scope of the accompanying claims will be apparent to the skilled reader.

What is claimed is:

1. A wound dressing comprising:
   an absorbent layer;
   an envelope formed from thermoplastic film enclosing said absorbent layer wherein the film has a textured performed surface on a front side of said envelope and a smoothed perforated surface on a rear side of said envelope;
   a semipermeable backing sheet covering said rear side of said envelope and extending outwardly therefrom; and
   a layer of adhesive on said backing sheet adjacent to said rear side of said envelope and bonding said envelope to said backing sheet.

2. A wound dressing according to claim 1, wherein said absorbent layer comprises a layer of a hydrophilic foam.

3. A wound dressing according to claim 1, wherein the absorbent layer has a basis weight in the range of 50–500 g/m$^2$.

4. A wound dressing according to claim 3, wherein the absorbent layer has a basis weight in the range of 100–400 g/m$^2$.

5. A wound dressing according to claim 1, wherein the absorbent layer has a free (uncompressed) liquid absorbency for physiological saline at 25° C. of from 5 to 30 g/g.

6. A wound dressing according to claim 1, wherein said thermoplastic film is formed from ethylene methyl acrylate (EMA).

7. A wound dressing according to claim 1, wherein said thermoplastic film is a mesh perforated film.

8. A wound dressing according to claim 7, wherein said film has from 5 to 50 perforations/cm$^2$.

9. A wound dressing according to claim 7, wherein said perforations have an area of from 0.01 to 2.0 mm$^2$.

10. A wound dressing according to claim 1, wherein said thermoplastic film has a basis weight of from 1 to 500 g/m$^2$.

11. A wound dressing according to claim 10, wherein said thermoplastic film has a basis weight of from 10 to 200 g/m$^2$.

12. A wound dressing according to claim 1, wherein said envelope is formed from a single piece of said thermoplastic film wrapped around said absorbent layer.

13. A wound dressing according to claim 1, wherein said backing sheet comprises a microporous polyurethane film.

14. A wound dressing according to claim 1 wherein said backing sheet has a water vapor permeability of from 300 to 5000 g/m$^2$/24 hrs at 37.5° C. at a humidity difference of 10% to 100%.

15. A wound dressing according to claim 14, wherein said backing sheet has a water vapor permeability of from 500 to 2000 g/m$^2$/24 hrs at 37.5° C. at a humidity difference of 10% to 100%.

16. A wound dressing according to claim 1, wherein said adhesive layer extends outwardly from said envelope to form an adhesive margin around said envelope for attachment of said wound dressing to a surface.

17. A wound dressing according to claim 1, wherein said adhesive layer has a basis weight of from 20 to 250 g/m$^2$.

18. A wound dressing according to claim 17, wherein said adhesive layer has a basis weight of from 50 to 150 g/m$^2$.

19. A wound dressing according to claim 1, further comprising one or more release coated cover sheets covering said front side of said envelope and said layer of adhesive.

20. A wound dressing according to claim 1 which is sterile and packaged in a microorganism-impermeable pouch.

21. A process for the production of a wound dressing comprising the steps of:
   providing a layer of absorbent material;
   wrapping said layer in an envelope of a textured perforated thermoplastic film; followed by
   smoothing said thermoplastic film on one side of said envelope; and
   applying an adhesive-coated backing sheet onto said smoothed thermoplastic film on said one side of said envelope.

22. A wound dressing prepared according to the process of claim 21.

23. A process according to claim 21, wherein said step of wrapping comprises wrapping a single sheet of said textured perforated thermoplastic film around said absorbent layer such that first and second longitudinal edges of said textured perforated thermoplastic film overlap, and bonding together said overlapping edges to form said envelope.

24. A process according to claim 21, wherein said step of smoothing comprises blowing hot air onto said one side of said envelope.

25. A process according to claim 24, wherein said step of smoothing further comprises measuring the temperature of the film and regulating said hot air blowing to control the maximum temperature reached by the film.

26. An apparatus for use in a process according to claim 24, said apparatus comprising:

a conveyor for conveying a layer of absorbent material enclosed between two layers of perforated textured thermoplastic film;

a hot air blower configured to blow hot air onto one of said layers of thermoplastic film to soften and flatten said one of said layers thereby smoothing said one of said layers;

a temperature sensor to measure the temperature of the said one of said layers adjacent to said hot air blower; and control means connected to said temperature sensor to regulate said conveyor and/or said hot air blower in response to signals from said temperature sensor.

27. An apparatus according to claim 26, wherein said temperature sensor is an infrared radiation detector.

28. An apparatus according to claim 26, wherein said hot air blower is adapted to blow hot air at a temperature between the softening temperature of the thermoplastic film and the melting temperature the thermoplastic film.

29. An apparatus according to claim 28, wherein said thermoplastic film is an ethylene methyl acrylate film and said hot air blower is adapted to blow hot air at a temperature between 110° C. and 160° C.

30. A process according to claim 21, further comprising the step of cutting said envelope into lengths prior to applying said adhesive-coated backing sheet.

31. A process according to claim 26, further comprising a step of cooling said envelope intermediate said smoothing and said cutting steps.

* * * * *

UNITED STATES PATENT AND TRADEMARK OFFICE
CERTIFICATE OF CORRECTION

PATENT NO. : 6,566,577 B1
DATED : May 20, 2003
INVENTOR(S) : Deborah Addison et al.

It is certified that error appears in the above-identified patent and that said Letters Patent is hereby corrected as shown below:

Title page,
Item [57], ABSTRACT,
Line 2, delete "a" and insert -- or --;
Line 10, delete "island an" and insert -- (7) on --;

Column 1,
Line 21, delete "is" and insert -- in --;
Line 51, delete "lays," and insert -- layers, --;
Line 54, delete "provides" and insert -- provide --;
Line 66, delete "as" and insert -- an --;

Column 2,
Line 4, delete "provides" and insert -- provide --;
Line 60, delete "island" and insert -- or --;

Column 3,
Line 20, delete "island" and insert -- from --;
Line 31, delete "wound" and insert -- around --;
Line 32, delete "sa" and insert -- so --;

Column 4,
Line 17, after "coated" insert -- cover --;
Line 36, delete "from" and insert -- front --;
Line 39, after "contrast" insert -- , --;
Line 46, delete "lays" and insert -- layer --;
Line 55, delete "an" and insert -- as --;
Line 59, delete "in" and insert -- its --;

UNITED STATES PATENT AND TRADEMARK OFFICE
CERTIFICATE OF CORRECTION

PATENT NO. : 6,566,577 B1
DATED : May 20, 2003
INVENTOR(S) : Deborah Addison et al.

It is certified that error appears in the above-identified patent and that said Letters Patent is hereby corrected as shown below:

Column 5,
Lines 3 and 5, delete "an" and insert -- as --;
Lines 9, 22, 23 and 48, delete "is" and insert -- in --;
Line 13, delete "lays" and insert -- layer --;
Line 17, delete "sheer" and insert -- sheet --;
Line 42, delete "or" and insert -- of --.

Signed and Sealed this

Sixth Day of April, 2004

JON W. DUDAS
*Acting Director of the United States Patent and Trademark Office*